United States Patent
Forsell

(10) Patent No.: US 9,427,301 B2
(45) Date of Patent: Aug. 30, 2016

(54) DURABLE IMPLANT

(76) Inventor: Peter Forsell, Zug (CH)

( * ) Notice: Subject to any disclaimer, the term of this patent is extended or adjusted under 35 U.S.C. 154(b) by 973 days.

(21) Appl. No.: 10/522,540

(22) PCT Filed: Jun. 19, 2003

(86) PCT No.: PCT/SE03/01055
§ 371 (c)(1),
(2), (4) Date: Aug. 22, 2005

(87) PCT Pub. No.: WO2004/011051
PCT Pub. Date: Feb. 5, 2004

(65) Prior Publication Data
US 2006/0111791 A1    May 25, 2006

Related U.S. Application Data

(60) Provisional application No. 60/398,825, filed on Jul. 29, 2002.

(51) Int. Cl.
*A61F 2/02* (2006.01)
*A61L 27/28* (2006.01)
*A61L 27/50* (2006.01)

(52) U.S. Cl.
CPC .................. *A61F 2/02* (2013.01); *A61L 27/28* (2013.01); *A61L 27/50* (2013.01)

(58) Field of Classification Search
CPC ............... A61F 2/0031; A61F 2/0004; A61F 2310/00437; A61F 2002/30069; A61F 2002/3007; A61F 2/82; A61F 2/02

USPC ........ 623/23.67, 1.49, 1.13, 1.42, 1.44–1.46, 623/4.49

See application file for complete search history.

(56) References Cited

U.S. PATENT DOCUMENTS

| | | |
|---|---|---|
| 2,060,913 A | 11/1936 | Weaver |
| 2,795,641 A | 6/1957 | Rowell |
| 3,209,081 A | 9/1965 | Ducote et al. |
| 3,731,679 A | 5/1973 | Wilhelmson et al. |
| 3,750,194 A | 8/1973 | Summers |
| 3,817,237 A | 6/1974 | Bolduc |
| 3,855,122 A | 12/1974 | Bourganel |
| 3,875,928 A | 4/1975 | Angelchik |
| 3,954,102 A | 5/1976 | Buuck |
| 4,009,711 A | 3/1977 | Uson |

(Continued)

FOREIGN PATENT DOCUMENTS

| | | | |
|---|---|---|---|
| DE | 19511998 | 10/1996 | |
| DE | 200 04 915 U1 | 8/2001 | ............. A61L 27/04 |

(Continued)

OTHER PUBLICATIONS

Database WPI; Week 199629; Derwent Publications Ltd., London, GB; AN 1996-279360.

(Continued)

*Primary Examiner* — Christopher D Prone

(57) ABSTRACT

An implant for use inside a human body including a biocompatible self-supporting base material, such as silicone, having surfaces exposed to aggressive body cells, when the implant is implanted in the human body. A cell barrier coating, such as Parylene® or a biocompatible metal, is coated on the surfaces of the base material to prevent body cells from breaking down the base material.

8 Claims, 2 Drawing Sheets

(56) References Cited

U.S. PATENT DOCUMENTS

Figure 1:
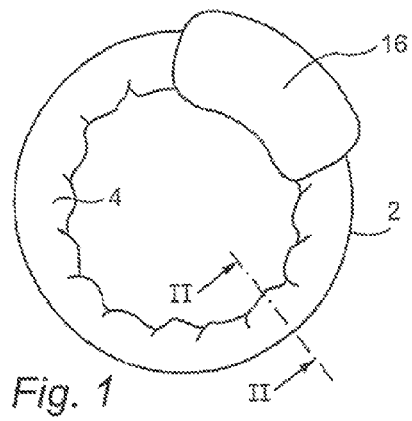

| | | |
|---|---|---|
| 4,026,305 A | 5/1977 | Brownlee et al. |
| 4,201,202 A | 5/1980 | Finney et al. |
| 4,235,222 A | 11/1980 | Ionescu |
| 4,243,306 A | 1/1981 | Bonini |
| 4,246,893 A | 1/1981 | Berson |
| 4,318,396 A | 3/1982 | Finney |
| 4,342,308 A | 8/1982 | Trick |
| 4,369,771 A | 1/1983 | Trick |
| 4,412,530 A | 11/1983 | Burton |
| 4,424,807 A | 1/1984 | Evans |
| 4,428,365 A | 1/1984 | Hakky |
| 4,480,642 A | 11/1984 | Stoy et al. |
| 4,517,967 A * | 5/1985 | Timm et al. ............... 600/40 |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,592,339 A | 6/1986 | Kuzmak et al. |
| 4,592,355 A | 6/1986 | Antebi |
| 4,602,621 A | 7/1986 | Hakky |
| 4,664,100 A | 5/1987 | Rudloff |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,941,461 A | 7/1990 | Fischell |
| 4,942,668 A | 7/1990 | Franklin |
| 4,955,907 A * | 9/1990 | Ledergerber ............... 623/8 |
| 4,958,630 A | 9/1990 | Rosenbluth et al. |
| 4,982,731 A | 1/1991 | Lue et al. |
| 5,012,822 A | 5/1991 | Schwarz |
| 5,042,084 A | 8/1991 | Daly |
| 5,062,416 A | 11/1991 | Stucks |
| 5,067,491 A | 11/1991 | Taylor, II et al. ............ 128/748 |
| 5,074,868 A | 12/1991 | Kuzmak |
| 5,160,338 A | 11/1992 | Vincent |
| 5,226,429 A | 7/1993 | Kuzmak |
| 5,304,206 A | 4/1994 | Baker, Jr. et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,509,888 A | 4/1996 | Miller |
| 5,518,504 A | 5/1996 | Polyak |
| 5,540,731 A | 7/1996 | Testerman |
| 5,578,069 A | 11/1996 | Miner, II |
| 5,601,604 A | 2/1997 | Vincent |
| 5,704,893 A | 1/1998 | Timm |
| 5,749,909 A | 5/1998 | Schroeppel et al. |
| 5,769,877 A | 6/1998 | Barreras |
| 5,771,903 A | 6/1998 | Jakobsson |
| 5,823,991 A | 10/1998 | Shim |
| 5,873,904 A * | 2/1999 | Ragheb et al. ............... 623/1.13 |
| 5,900,909 A | 5/1999 | Parulski et al. |
| 5,910,149 A | 6/1999 | Kuzmak |
| 5,938,584 A | 8/1999 | Ardito et al. |
| 5,938,669 A | 8/1999 | Klaiber et al. |
| 5,978,712 A | 11/1999 | Suda et al. |
| 6,042,608 A | 3/2000 | Ishikawa et al. |
| 6,067,991 A | 5/2000 | Forsell |
| 6,074,341 A | 6/2000 | Anderson et al. |
| 6,083,930 A | 7/2000 | Roufa et al. |
| 6,102,922 A | 8/2000 | Jakobsson et al. |
| 6,117,067 A | 9/2000 | Gil-Vernet |
| 6,135,945 A | 10/2000 | Sultan |
| 6,162,238 A | 12/2000 | Kaplan et al. |
| 6,185,452 B1 | 2/2001 | Schulman et al. |
| 6,210,347 B1 | 4/2001 | Forsell |
| 6,221,060 B1 | 4/2001 | Willard |
| 6,287,315 B1 | 9/2001 | Wijeratne et al. |
| 6,319,191 B1 | 11/2001 | Sayet et al. |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,558,315 B1 | 5/2003 | Kuyava |
| 6,638,208 B1 | 10/2003 | Natarajan et al. |
| 6,709,385 B2 | 3/2004 | Forsell |
| 6,895,280 B2 | 5/2005 | Meadows et al. |
| 6,915,165 B2 | 7/2005 | Forsell |
| 6,929,625 B2 | 8/2005 | Bierman |
| 6,953,429 B2 | 10/2005 | Forsell |
| 7,011,624 B2 | 3/2006 | Forsell |
| 7,017,583 B2 | 3/2006 | Forsell |
| 7,207,936 B2 | 4/2007 | Forsell |
| 7,235,044 B2 | 6/2007 | Forsell |
| 7,250,037 B2 | 7/2007 | Shermer et al. |
| 7,338,437 B2 | 3/2008 | Forsell |
| 7,367,938 B2 | 5/2008 | Forsell |
| 7,371,208 B2 | 5/2008 | Forsell |
| 7,407,479 B2 | 8/2008 | Forsell |
| 7,407,481 B2 | 8/2008 | Forsell |
| 7,442,165 B2 | 10/2008 | Forsell |
| 7,621,863 B2 | 11/2009 | Forsell |
| 7,648,455 B2 | 1/2010 | Forsell |
| 7,666,132 B2 | 2/2010 | Forsell |
| 2001/0011543 A1 | 8/2001 | Forsell |
| 2002/0091395 A1 | 7/2002 | Gabbay |
| 2002/0099438 A1 * | 7/2002 | Furst ............................ 623/1.16 |
| 2002/0182392 A1 | 12/2002 | Welch, Jr. et al. ............ 428/216 |
| 2002/0183588 A1 | 12/2002 | Fierro |
| 2003/0009221 A1 | 1/2003 | Forsell |
| 2003/0032857 A1 | 2/2003 | Forsell |
| 2003/0060893 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093141 A1 | 5/2003 | Dimatteo et al. ............ 623/1.13 |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Peter |
| 2004/0034275 A1 | 2/2004 | Forsell |
| 2004/0133219 A1 | 7/2004 | Forsell |
| 2004/0177918 A1 | 9/2004 | Murata et al. |
| 2006/0094926 A1 | 5/2006 | Forsell |
| 2006/0111791 A1 | 5/2006 | Forsell |
| 2006/0142635 A1 | 6/2006 | Forsell |
| 2006/0149124 A1 | 7/2006 | Forsell |
| 2006/0149125 A1 | 7/2006 | Forsell |
| 2006/0167337 A1 | 7/2006 | Forsell |
| 2006/0235482 A1 | 10/2006 | Forsell |
| 2007/0015959 A1 | 1/2007 | Forsell |
| 2007/0073099 A1 | 3/2007 | Forsell |
| 2007/0232848 A1 | 10/2007 | Forsell |
| 2008/0045783 A1 | 2/2008 | Forsell |
| 2008/0200753 A1 | 8/2008 | Forsell |
| 2008/0275296 A1 | 11/2008 | Forsell |
| 2009/0018388 A1 | 1/2009 | Forsell |
| 2009/0054725 A1 | 2/2009 | Forsell |
| 2009/0240100 A1 | 9/2009 | Forsell |
| 2009/0250068 A1 | 10/2009 | Forsell |

(56) References Cited

U.S. PATENT DOCUMENTS

| | | |
|---|---|---|
| 2010/0145138 A1 | 6/2010 | Forsell |
| 2010/0145139 A1 | 6/2010 | Forsell |
| 2010/0217067 A1 | 8/2010 | Forsell |

FOREIGN PATENT DOCUMENTS

| | | | | |
|---|---|---|---|---|
| EP | 0200286 | 11/1986 | | |
| EP | 0626154 A1 | 11/1994 | | |
| EP | 0 679 373 A2 | 11/1995 | ................ | A61F 2/06 |
| EP | 0 716 834 A1 | 6/1996 | ................ | A61F 2/04 |
| EP | 0 747 069 | 12/1996 | ............. | A61L 29/00 |
| EP | 1072238 | 1/2001 | | |
| FR | 2688693 | 9/1993 | | |
| FR | 2692777 | 12/1993 | | |
| FR | 2 717 069 A1 | 9/1995 | ................ | A61F 2/01 |
| FR | 2717069 | 9/1995 | | |
| FR | 27565485 | 6/1998 | | |
| FR | 2797181 | 2/2001 | | |
| SU | 906-526 | 2/1982 | | |
| WO | 94/27504 | 12/1994 | | |
| WO | 96/01597 | 1/1996 | | |
| WO | 96/11036 | 4/1996 | | |
| WO | 97/41799 | 11/1997 | | |
| WO | 00/09048 | 2/2000 | | |
| WO | 00/15158 | 3/2000 | | |
| WO | 0112078 | 2/2001 | | |
| WO | 01/47431 | 7/2001 | | |
| WO | 01/47434 | 7/2001 | | |
| WO | 01/47435 | 7/2001 | | |
| WO | WO0167996 A2 * | 9/2001 | ................ | A61F 2/26 |
| WO | 2004/012806 | 2/2004 | | |

OTHER PUBLICATIONS

International Search Report from International Application No. PCT/SE03/01055, mailed Sep. 22, 2003.
European Office Action for Application No. 03 733 775.5-1219, Dated Jun. 22, 2010.
European Communication pursuant to Article 94(3) EPC, dated Jun. 22, 2010; Application No. 03 733 775.5-1219.
NPC-102 N Medical Angioplasty Sensor web page at www.novasensor.com/catalog/NPC_102.html and NPC-102 Datasheet, circa 1997, retrieved from the Internet Archives for www.novasensor.com.
Webster's II New River side University, 1984, pp. 573,1000.
U.S. Appl. No. 11/988,450, Forsell.
U.S. Appl. No. 12/839,115; Forsell.
U.S. Appl. No. 12/839,162; Forsell.
U.S. Appl. No. 12/859,454; Forsell.
U.S. Appl. No. 09/373,224; Forsell.

* cited by examiner

DURABLE IMPLANT

This application is the U.S. National Phase of Application No. PCT/SE2003/001055, which designated the U.S., and claims the benefit of Provisional Application No. 60/398,825, filed Jul. 29, 2002, the entire contents of which are hereby incorporated by reference in this application.

The present invention relates to an implant for use inside a human body.

There is a great variety of implants for use inside the human body. A typical biocompatible material generally used or making these implants is silicone. Making implants of silicone is most beneficial for reasons of production and function. However, It has been indicated that silicone might be involved in diseases that create fibrosis—such as SLE (Systemic Lupus Erythematosus), although there is no evidence that this is the case. It is established, however, especially from breast-implants, that silicone implants in the human body do not last for ever—50% of implanted silicone implants were broken after 15 years, according to a large article published in the Lancet a couple of years ago. This indicates that the human body, at least to some extent, might break down the silicone material. Many other materials used for implants, like polyurethane, Teflon may have the same problem.

The object of the present invention is to provide a durable implant with a long lifetime.

Accordingly, the present invention provides an implant for use inside a human body, comprising a biocompatible self-supporting base material having surfaces exposed to aggressive body cells, when the implant is implanted in the human body, characterised by a cell barrier coating coated on the surfaces to prevent body cells from breaking down the base material.

Generally, the base material comprises hard silicone, typically having a hardness of at least 60 Shure.

In research by the inventor he has found small histological silicone particles in the fat around implanted silicone implants. Based on these facts the inventor has concluded that the human body with the macrophages in the frontline slowly destroys silicone, which could explain the occurrence of silicone particles in the fat surrounding the implants. It is well known that foreign material, like silicone, creates an active fibrosis surrounding the foreign material. Therefore, if histological particles were spread out these would most likely also create fibrosis around them. To prevent histological silicone particles from spreading in the human body, and perhaps follow the lymphatic passageway, the inventor has realized that a barrier coating, which cannot be penetrated by body cells would protect the silicone implant from the body cells.

Preferably, the cell barrier coating comprises a PARYLENE® coating, or a biocompatible metal coating, such as gold, silver or titanium.

Advantageously, the implant comprises a property improving means for improving at least one physical property of the implant other than self-supporting and cell barrier properties. For example, the property improving means may comprise a core of a viscoelastic material, such as silicone gel, cellulose gel or collagen gel, covered with the self-supporting base material.

The property improving means may also comprise a fatigue resistant material. For example, the base material may form a first layer covered with a second layer, such as a polyurethane layer, that is more fatigue resistant than the first layer.

The property improving means may also comprise gas, such as air, contained in a multiplicity of cavities formed in the base material to improve the flexibility of the base material. In this case TEFLON® advantageously constitutes the base material, The cavities may be defined by net strutures of the TEFLON® material.

In an embodiment of the invention, the base material forms an inflatable tubing. The tubing may have an inner surface defining the interior of the tubing, wherein the coating covers the inner surface. In accordance with an alternative, the base material may form two coaxial tubular layers of the tubing and the property improving means may comprise a tubular intermediate layer of the viscoelastic material, which is located between the coaxial tubular layers. In accordance with another alternative, the base material may form an outer tubular layer and an inner arcuate layer attached to the outer tubular layer, so that the outer and inner layers define a curved space extending longitudinally along the tubing, wherein the property improving means comprises viscoelastic material filling the space. In accordance with yet another alternative, the base material forms an inflatable tubing and the property improving means comprises a liquid impermeable coating coated on the base material. The coating may be coated on the external and/or internal surface of the tubing. Preferably, the liquid impermeable coating comprises a PARYLENE® coating, or a biocompatible metal coating. Where hard silicone, which is a liquid semi-permeable material, constitutes the base material, the coating of PARYLENE® or metal gives the advantage that the tubing may be inflated by hydraulic fluid under pressure without risking fluid diffusing through the silicone wall of the tubing.

The barrier coating may comprise a composite of different materials to achieve the cell-barrier protection as described above. There are several examples of such composite materials on the market, for example a composite of polyurethane and silicone called ELASTON®.

Figure 2:
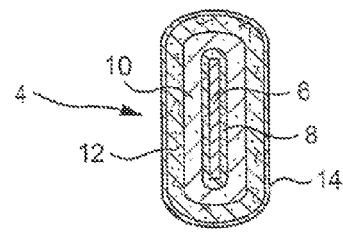
Figure 3:
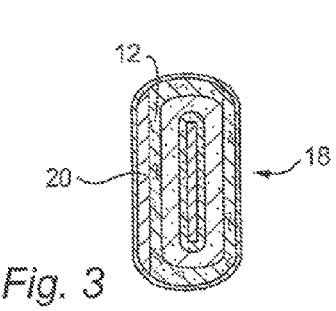
Figure 3A:
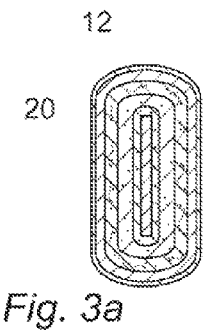
Figure 4:
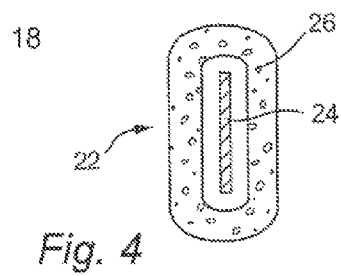
Figure 5:
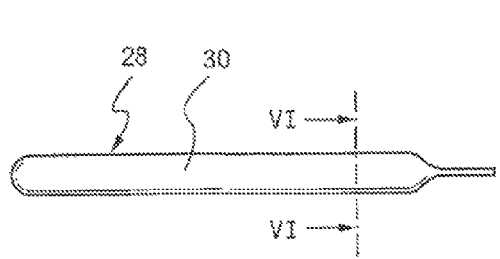
Figure 6:
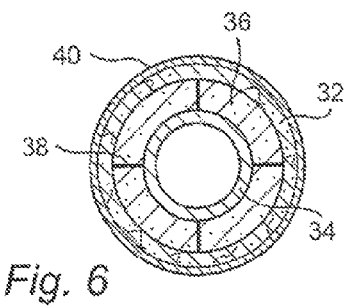
Figure 9:
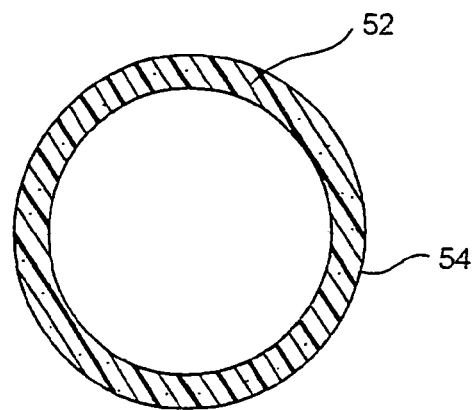
Figure 10:
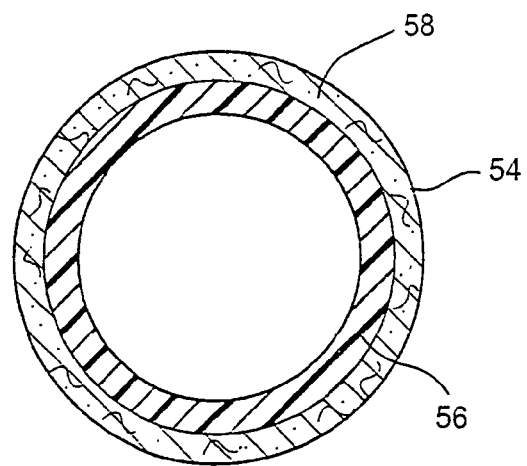
Figure 11:
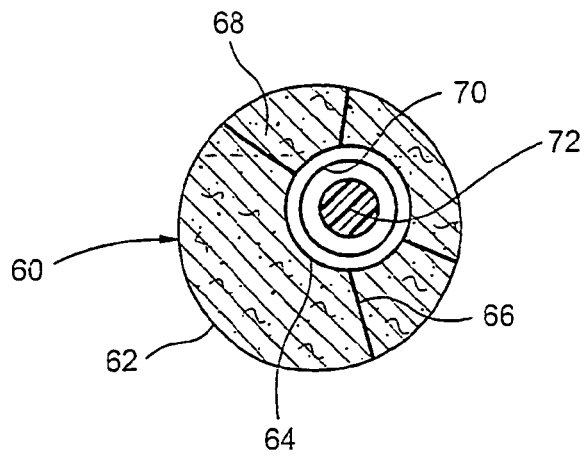

The invention is described in more detail in the following with reference to the accompanying drawings, in which:

FIG. 1 is a front view of an implant according to the present invention in the form of mechanical constriction device, FIG. 2 is an enlarged cross-section along the line II-II in FIG. 1, FIGS. 3, 3A and 4 are modifications of the embodiment shown in FIG. 2, FIG. 5 is a front view of an implant according to the invention in the form of a hydraulic constriction device, FIG. 6 is an enlarged cross-section along the line VI-VI in FIG. 5, FIGS. 7-10 are modifications of the embodiment shown in FIG. 6, and FIG. 11 is a modification of the embodiment shown in FIG. 2.

Referring to the drawing figures, like reference numerals designate identical or corresponding elements throughout the several figures.

FIG. 1 illustrates an implant according to the present invention in the form of a mechanical constriction device 2 comprising an elongate composite structure 4 adapted to extend around and constrict the stomach or esophagus of an obese patient to form a restricted stoma opening therein. Referring to FIG. 2, the elongate composite structure 4 comprises a strong band 6 of nylon or the like, a tubular layer 8 of hard silicone, in which the band 6 slides, a soft layer 10 of a viscoelastic material, here a silicone gel having a hardness not more than 20 Shure, encircling the hard silicone layer 8, and a tubular layer 12 of a self-supporting base material of hard silicone having a hardness of at least 60 Shure, surrounding the soft silicon layer 10. A barrier coating 14 of PARYLENE® or a biocompatible metal, such as gold, silver or titanium, is coated on the outer hard silicone layer 12 to prevent body cells from attacking the silicone. A coating of TEFLON® or the like may also be coated on the internal surface of the inner tubular hard silicone layer 8 to reduce the friction between the nylon band 6 and the layer 8. The constriction device 2 has an adjustment means 16 that can displace the end portions of the nylon band 6 relative to each other to either enlarge or constrict the stoma opening.

FIG. 3 shows an elongate composite structure 18 similar to that of FIG. 2, except that a layer 20 of a fatigue resistant material, here polyurethane, is applied on the hard silicone layer 12 along the inner side of the structure 18 that is intended to contact the stomach or esophagus. Alternatively, the layer 20 may be tubular and surround the layer 12, see FIG. 3A.

FIG. 4 shows a cross-section of an elongate composite structure 22 of an embodiment of the invention, in which the self-supporting base material comprises poly(tetrafluoroethylene) ("PTFE"), also known by the trade name self-supporting base material comprises TEFLON®. The base material forms a longitudinal cavity in which a strong nylon band 24 slides. Property improving means in the form of gas, here air, contained in a multiplicity of cavities 26 are formed in the base material to improve the flexibility thereof. The external surface of the composite structure is coated with a cell barrier coating.

FIG. 5 shows an implant according to the invention in the form of a hydraulic constriction device 28 comprising an elongate composite structure in the form of an inflatable tubing 30, in which the base material of hard silicone forms an outer tubular layer 32 and an inner coaxial layer 34. A viscoelastic material, here soft silicone gel, forms an intermediate layer 36 located between the tubular layers 32, 34. Four longitudinal partition walls 38 between the tubular layers 32, 34 divide the intermediate layer 36 into four sections to prevent the silicone gel from displacing in the circumferential direction of the tubing 30. (Also the embodiments according to FIGS. 2 and 3 may be provided with such longitudinal partition walls.) The outer layer 32 is coated with a barrier coating 40 of PARYLENE® or metal. Also the inner layer 34 may be coated with a coating of PARYLENE® or metal. If a PARYLENE® or metal coating is chosen the composite structure will be completely liquid impermeable.

Figure 7:
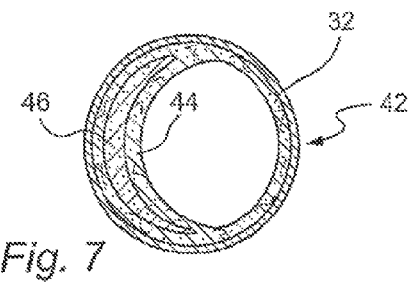

FIG. 7 shows a tubing 42 similar to that of FIG. 6, except that an inner arcuate layer 44 is substituted for the inner tubular layer 34. The arcuate layer 44 is attached to the outer tubular layer 32, so that the outer tubular layer 32 and the arcuate layer 44 define a curved space extending longitudinally along the tubing 42. A viscoelastic material, here silicone gel 46, fills the space. In this embodiment there is no need for partition walls of the kind shown in the embodiment according to FIG. 6. The tubing 42 is intended to be applied around the stomach or esophagus so that the space with the protecting soft silicone gel 46 is located close to the stomach or esophagus.

As taught by the embodiment of FIG. 7, in the composite structures shown in FIGS. 2 and 3 the soft silicone gel may alternatively be applied in a longitudinal space close to the inner side of the elongate composite structure 4 and 18, respectively, that is intended to contact the stomach or esophagus.

In the same manner as described above in connection with the embodiment of FIG. 3, a layer of a fatigue resistant material, here polyurethane, may be applied on the outer tubular layer 32 of hard silicone of the tubing 30 and 42, respectively, along the side of the tubing 30 and 42, respectively, that is intended to contact the stomach or esophagus, when the tubing 30 and 42, respectively, encircles the stomach or esophagus.

Figure 8:
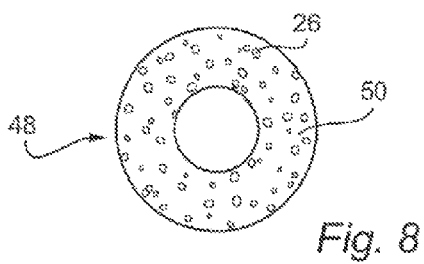

FIG. 8 shows a cross-section of an elongate composite structure 48 of an embodiment of the invention, in which TEFLON® constitutes the self-supporting base material, which is formed to an inflatable tubing 50. Property improving means in the form of gas contained in a multiplicity of cavities 26 are formed in the base material to improve the flexibility of the tubing 50. The external surface of the composite structure is coated with a cell barrier coating.

FIG. 9 shows a cross-section of a tubular composite structure of an embodiment of the invention, in which the self-supporting base material 52 is made of a polymer material suited for implantation, for example silicone or polyurethane. A cell barrier coating 54, for example made of PARYLENE® or metal, is applied on the external surface or on both the external and internal surfaces of the tubular structure FIG. 10 shows the same embodiment as FIG. 9 except that the base material comprises a layer 56 of polyurethane surrounded by a layer 58 of silicone.

FIG. 11 shows a cross-section of a mechanical constriction device of another embodiment of the invention, comprising a double-walled tubing 60 of a self-supporting base material of hard silicone. The tubing 60 has an external wall 62 and an internal wail 64 spaced from the external wall 62, partition walls 66 dividing the space between the external and internal walls 62 and 64, respectively, of the tubing 60 into longitudinal cells 68, which are filled with a soft viscoelastic material, for example silicone gel. The internal wall 64 is coated with a friction reducing coating 70, for example made of TEFLON® or the like. A strong band 72 of nylon or the like slides in the tubing 60 on the friction reducing coating 70 to enable adjustment of the constriction device in the same manner as described above in connection with the embodiment according to FIGS. 1 and 2. The external surface of the composite structure is coated with a cell barrier coating.

Although the present invention has been described in terms of particular embodiments, it is not intended that the invention be limited to those embodiments. Modifications of the embodiments within the spirit of the invention will be apparent to those skilled in the art. The scope of the invention is defined by the claims that follow.

The invention claimed is:

1. An implant for use inside a human body comprising a composite structure adapted to extend around and constrict a tubular organ of the human body, comprising:
   a biocompatible self-supporting base material comprising a layer of polyurethane surrounded by a layer of silicone and having surfaces adapted to be exposed to aggressive body cells, when the implant is implanted in the human body,
   a cell barrier coating comprising a poly(p-xylylene) polymer or a biocompatible metal coating that is coated on said base material surfaces and adapted to prevent body cells from breaking down said base material when the implant is implanted in the human body or for improving at least one physical property of the composite structure other than the composite structure being self-supporting.

2. The implant according to claim 1, further comprising a viscoelastic material covered by the base material, which comprises silicone gel, cellulose gel or collagen gel.

3. The implant according to claim 2 further comprising a band of nylon and a second, tubular layer of silicone in which the band slides, the band of nylon and the second, tubular layer of silicone being surrounded by the layer of viscoelastic material.

4. The implant according to claim 2, wherein the viscoelastic material is a silicone gel having a hardness of not more than 20 Shure.

5. The implant according to claim 2, wherein the silicone layer of the base material is a hard silicone having a hardness of at least 60 Shure.

6. The implant according to claim 2, wherein the cell barrier coating is a biocompatible metal coating comprising gold, or titanium.

7. An implant for use inside a human body comprising a composite structure adapted to extend around and constrict a tubular organ of the human body, comprising:
- a biocompatible self-supporting base material comprising a layer of polyurethane and a layer of silicone and having surfaces adapted to be exposed to aggressive body cells, when the implant is implanted in the human body,
- a cell barrier coating comprising a poly(p-xylylene) polymer or a biocompatible metal coating that is coated on said base material surfaces and adapted to prevent body cells from breaking down said base material when the implant is implanted in the human body or for improving at least one physical property of the composite structure other than the composite structure being self-supporting,
- further comprising a viscoelastic material covered by the base material, which viscoelastic material comprises a silicone gel having a hardness of not more than 20 Shure.

8. An implant for use inside a human body comprising a composite structure adapted to extend around and constrict a tubular organ of the human body, comprising:
- a biocompatible self-supporting base material comprising a layer of polyurethane and a layer of silicone and having surfaces adapted to be exposed to aggressive body cells, when the implant is implanted in the human body,
- a cell barrier coating comprising a poly(p-xylylene) polymer or a biocompatible metal coating that is coated on said base material surfaces and adapted to prevent body cells from breaking down said base material when the implant is implanted in the human body or for improving at least one physical property of the composite structure other than the composite structure being self-supporting,
- further comprising a viscoelastic material covered by the base material, which comprises silicone gel, cellulose gel or collagen gel,
- wherein the silicone layer of the base material is a hard silicone having a hardness of at least 60 Shure.

* * * * *